(12) United States Patent
Hudson et al.

(10) Patent No.: US 9,399,018 B2
(45) Date of Patent: Jul. 26, 2016

(54) IMPLANT DEVICES THAT DIFFER BY RELEASE PROFILE AND METHODS OF MAKING AND USING SAME

(75) Inventors: Bruce W. Hudson, Pleasant Grove, AL (US); Peter Markland, Birmingham, AL (US)

(73) Assignee: Evonik Corporation, Parsippany, NJ (US)

( * ) Notice: Subject to any disclaimer, the term of this patent is extended or adjusted under 35 U.S.C. 154(b) by 257 days.

(21) Appl. No.: 12/883,415

(22) Filed: Sep. 16, 2010

(65) Prior Publication Data

US 2011/0142906 A1 Jun. 16, 2011

Related U.S. Application Data

(60) Provisional application No. 61/243,303, filed on Sep. 17, 2009.

(51) Int. Cl.
| | |
|---|---|
| *A61K 9/14* | (2006.01) |
| *A61K 9/50* | (2006.01) |
| *A61K 9/00* | (2006.01) |
| *A61K 38/09* | (2006.01) |

(52) U.S. Cl.
CPC .............. *A61K 9/146* (2013.01); *A61K 9/0024* (2013.01); *A61K 9/5084* (2013.01); *A61K 38/09* (2013.01)

(58) Field of Classification Search
CPC ..... A61K 38/09; A61K 9/0024; A61K 9/146; A61K 9/5084
See application file for complete search history.

(56) References Cited

U.S. PATENT DOCUMENTS

| | | | |
|---|---|---|---|
| 4,720,384 A | 1/1988 | Di Luccio et al. |
| 4,794,001 A | 12/1988 | Mehta et al. |
| 4,874,612 A | 10/1989 | Deasy |
| 4,897,268 A | 1/1990 | Tice et al. |
| 4,976,949 A | 12/1990 | Meyer et al. |
| 5,035,891 A | 7/1991 | Runkel et al. |

(Continued)

FOREIGN PATENT DOCUMENTS

| | | |
|---|---|---|
| EP | 1374860 A1 | 1/2004 |
| JP | 1216917 A | 8/1989 |

(Continued)

OTHER PUBLICATIONS

Blanco-Príeto, M. et al., "Importance of single or blended polymer types for controlled in vitro release and plasma levels of a somatostatin analogue entrapped in PLA/PLGA microspheres," J Control Release, 2004, 96: 437-448.

(Continued)

*Primary Examiner* — Aradhana Sasan
(74) *Attorney, Agent, or Firm* — Linda S. Li; Jason S. Ngui; Bernard Lau (57) ABSTRACT

Described herein are implant devices, kits comprising the implant devices, and methods of making and using the devices and kits. In one aspect, a plurality of implant devices comprises at least two implants that exhibit a different release profile of a bioactive agent. In another aspect, an implant device comprises one or more adjoined polymer bodies, wherein at least two of the polymer bodies provide a different release profile of a bioactive agent. In another aspect, a kit comprises one or more disclosed implant devices. In another aspect, methods of delivering a bioactive agent to a subject comprise administering to the subject one or more disclosed implant devices.

11 Claims, 6 Drawing Sheets

(56) References Cited

U.S. PATENT DOCUMENTS

| | | |
|---|---|---|
| 5,153,002 A | 10/1992 | McMullen |
| 5,178,874 A | 1/1993 | Kwan et al. |
| 5,429,822 A | 7/1995 | Gresser et al. |
| 5,456,917 A | 10/1995 | Wise et al. |
| 5,702,716 A | 12/1997 | Dunn et al. |
| 5,705,191 A | 1/1998 | Price et al. |
| 5,750,143 A | 5/1998 | Rashid et al. |
| 5,876,452 A | 3/1999 | Athanasiou et al. |
| 5,958,458 A | 9/1999 | Norling et al. |
| 6,013,853 A | 1/2000 | Athanasiou et al. |
| 6,319,512 B1 | 11/2001 | Rothen-Weinhold et al. |
| 6,447,796 B1 | 9/2002 | Vook et al. |
| 6,479,065 B2 | 11/2002 | Jaworowicz et al. |
| 6,599,529 B1 | 7/2003 | Skinhøj et al. |
| 6,702,803 B2 | 3/2004 | Kupperblatt et al. |
| 6,793,938 B2 | 9/2004 | Sankaram |
| 6,844,010 B1 | 1/2005 | Setterstrom et al. |
| 6,855,331 B2 | 2/2005 | Vook et al. |
| 6,869,588 B2 | 3/2005 | Weller et al. |
| 6,902,743 B1 | 6/2005 | Setterstrom et al. |
| 6,923,988 B2 | 8/2005 | Patel et al. |
| 2002/0131988 A1 | 9/2002 | Foster et al. |
| 2003/0055075 A1 | 3/2003 | Rubsamen |
| 2004/0265383 A1 | 12/2004 | Cui et al. |
| 2005/0244447 A1 | 11/2005 | Heath |
| 2006/0029637 A1 | 2/2006 | Tice et al. |
| 2006/0159721 A1 | 7/2006 | Siegel et al. |
| 2008/0131484 A1 | 6/2008 | Robinson et al. |
| 2008/0254086 A1 | 10/2008 | Brown et al. |

FOREIGN PATENT DOCUMENTS

| | | |
|---|---|---|
| JP | H04-364120 A | 12/1992 |
| WO | WO-01/07079 A1 | 2/2001 |
| WO | WO-2005/107715 A1 | 11/2005 |

OTHER PUBLICATIONS

Kim, H. et al., "Comparative study on sustained release of human growth hormone from semi-crystalline poly(l-lactic acid) and amorphous poly(d,l-lactic-co-glycolic acid) microspheres: morphological effect on protein release," J Control Release, 2004, 98: 115-125.

Li, Y. and Zhu, J., "Modulation of combined-release behaviors from a novel "tablets-in-capsule system"," J Control Release, 2004, 95: 381-389.

Siepmann, N. et al., "Effect of the size of biodegradable microparticles on drug release: experiment and theory," J Control Release, 2004, 96: 123-134.

International Search Report and Written Opinion issued on Nov. 2, 2011 for Intl. App. No. PCT/US2010/049104, filed Sep. 16, 2010 (Inventor—Hudson et al.; Applicant—Surmodics Pharmaceuticals, Inc.; pp. 1-13).

International Preliminary Report on Patentability issued on Mar. 29, 2012 for Intl. App. No. PCT/US2010/049104, filed Sep. 16, 2010 (Inventor—Hudson et al.; Applicant—Evonik Degussa Corp.; pp. 1-8).

*Cumulative Goserelin released from formulations with similar drug loadings, but different polymers.*

Figure 3

Cumulative Goserelin released from formulations made with the same polymer, but different drug loadings.

Figure 4

*Cumulative Goserelin released from formulations made with varying drug loadings and polymers.*

Figure 5

Cumulative Goserelin released from formulations with varying drug loadings and polymers.

Figure 6

IMPLANT DEVICES THAT DIFFER BY RELEASE PROFILE AND METHODS OF MAKING AND USING SAME

CROSS REFERENCE TO RELATED APPLICATIONS

This application is based upon and claims the benefit of priority from prior U.S. Provisional Application No. 61/243,303, filed Sep. 17, 2009, the entire contents of which are incorporated herein by reference.

BACKGROUND

Implant formulations can be designed to release bioactive agents into a fluid or tissue of a subject. Useful formulations are those that comprise a polymer that releases the bioactive agent as the polymer biodegrades. One purpose of the polymer is to restrict the influx of water, which in turns controls the dissolution of the bioactive agent followed by the release of the bioactive agent from the implant. While the polymer provides a number of advantages, such as restricting water influx, it can be difficult to provide an appropriate polymer formulation that is effective to achieve a targeted or effective release profile. A variety of different release profiles are needed in the pharmaceutical arts that generally depend on variables in the subject to be treated and the particular characteristics of the disorder. Unfortunately, a typical drug-delivery strategy based on a single implant composition often fails to meet the needs of varying release profiles.

As such, a need exists for drug-delivery strategies that can effectively provide for a desired release profile without undue manufacturing limitations. These needs and other needs are satisfied by the present invention.

SUMMARY

Described herein are implant devices, kits comprising the implant devices, and methods of making and using the devices and kits. In one aspect, a plurality of implant devices comprises at least two implants that exhibit a different release profile of a bioactive agent. In another aspect, an implant device comprises one or more adjoined polymer bodies, wherein at least two of the polymer bodies provide a different release profile of a bioactive agent. In another aspect, a kit comprises one or more disclosed implant devices. In another aspect, methods of delivering a bioactive agent to a subject comprise administering to the subject one or more disclosed implant devices.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Before the present compounds, compositions, composites, articles, devices and/or methods are disclosed and described, it is to be understood that the aspects described below are not limited to specific compounds, compositions, composites, articles, devices, methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

An "implant device," as used herein, refers to a substantially solid device comprised of a polymer having a bioactive agent in and/or on a surface of the polymer. The implant devices can be any size. In some examples, the implant devices can be so sized as to fit within an injection device, such as a trochar. The implant devices can also comprise other additives, surface treatments, coatings, and the like. The implant devices can be administered to a subject through any appropriate route, including through injection, oral administration, and the like.

The term "biocompatible" refers a substance that is substantially non-toxic to a subject.

"Biodegradable" is generally referred to herein as a material that will erode to soluble species or that will degrade under physiologic conditions to smaller units or chemical species that are, themselves, non-toxic (biocompatible) to the subject and capable of being metabolized, eliminated, or excreted by the subject.

A "bioactive agent" refers to an agent that has biological activity. The biological agent can be used to treat, diagnose, cure, mitigate, prevent (i.e., prophylactically), ameliorate, modulate, or have an otherwise favorable effect on a disease, disorder, infection, and the like. A "releasable bioactive agent" is one that can be released from a disclosed polymer. Bioactive agents also include those substances which affect the structure or function of a subject, or a pro-drug, which becomes bioactive or more bioactive after it has been placed in a predetermined physiological environment.

A "release profile," as used herein, refers to the amount of bioactive agent that is released from the implant device over time. Thus, two or more implant devices or polymer bodies that differ by release profile will release a different amount of the same bioactive agent over time. Release profiles can be determined by measuring the amount of bioactive agent released over time using methods known in the art. When comparing the release profile of two different implant devices or polymer bodies, it can be useful to plot the amount of bioactive agent released from each device or body and compare each plot to determine if the two different implant devices or polymer bodies exhibit the same or different release profiles. Two or more devices or bodies that exhibit different release profiles will exhibit measurably different release profiles. For example, different release profiles can be characterized by a different amount of released (or remaining) bioactive agent at any point during the release. When comparing two or more implant devices or polymers, the amount of bioactive agent released at any point in time during the release can differ by at least 1%, 5%, 10%, 20%, 30%, 40%, 50%, 60%, or greater, including differences of 100% or more.

A "portion" of an implant device, as used herein, refers to a part of an implant device. When an implant device has "portions," at least two of the portions differ by release profile. In some examples, the "portion" refers to a cross-section of the implant device, a segment of the implant device, or a combination thereof. In a specific example, the "portion" refers to a cross-section of an implant device that comprises at least one other cross-sectional portion (e.g., two or four cross-sectional portions). In another specific example, the "portion" refers to a segment of an implant device that is defined by one or more ends, wherein at least one of the ends adjoins, i.e., is physically connected to, an end of another portion. Each segment can itself comprise one or more portions, such as cross-sections.

A "kit," as used herein, refers to a package containing one or more disclosed implant devices. The implant devices of the kit can optionally be present in a suitable pharmaceutical carrier. The packaging of the kit can be any suitable packaging material, such as a sterile package, a syringe, or a trochar, among others.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different polymers and agents are disclosed and discussed, each and every combination and permutation of the polymer and agent are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

The present invention relates to implant devices for achieving a desired release profile of a bioactive agent. In one aspect, a plurality of implant devices can be administered to a subject, wherein at least two of the implant devices provide a different release profile for a given bioactive agent. By using at least two implant devices that provide a different release profile than the other(s), the release profile of the plurality of implant devices will be different relative to a plurality of implant devices that all individually exhibit the same release profile, or relative to an individual implant device capable of exhibiting only a single release profile. When a plurality of implant devices are used in combination or are present together in a kit, the implant devices can have the same size and/or shape, or have a different size and/or shape.

In a further aspect, a plurality of modular polymer portions can be adjoined into a single implant device, wherein at least two of the polymer portions exhibit a different release profile. According to this aspect, formed polymer portions can be connected to each other to provide a single unit. In a similar aspect, an implant device can be prepared by co-manufacturing two or more polymers together into a single unit, wherein at least two of the polymers exhibit a different release profile. Such modular or co-manufactured single unit implant devices can in turn be used individually or in combination with other implant devices, depending on the desired release profile.

As will be appreciated, a large number of release profiles can be achieved through the present invention. Generally, the implant devices described herein allow for a variety of controlled-release, extended-release, modified-release, sustained-release, pulsatile-release, delayed-release, or programmed-release profiles that can be provided through the use of multiple implant devices, multiple polymer bodies that can be adjoined, or a combination thereof.

The implant device generally comprises one or more biodegradable polymer bodies having a releasable bioactive agent in or on a surface of the polymer body. Upon implanting the implant device into a subject, the bioactive agent is released from the polymer body, which then provides for a desired therapeutic result.

The polymer body of the implant device can comprise any suitable biocompatible and biodegradable or non-biodegradable polymer. The polymers can be homopolymers or copolymers, including block or blocky co- or ter-polymers, random co- or ter-polymers, star polymers, or dendrimers. Any desired molecular weight polymer can be used, depending on the desired properties of the polymer body. In certain aspects, if a high strength polymer body is desired, then high molecular weight polymers can be used, for example, to meet strength requirements. In other aspects, low or medium molecular weight polymers can be used when, for example, when resorption time of the polymer, rather than material strength is desired.

The molecular weight of a polymer can be important given that molecular weight influences the biodegradation rate of a biodegradable polymer. For a diffusional mechanism of bioactive agent release, the polymer should remain intact until all of the drug is released from the polymer and then degrade. The drug can also be released from the polymer as the polymer bioerodes. By an appropriate selection of polymeric materials, a polymer formulation can be made such that the resulting polymer exhibits both diffusional release and biodegradation release properties. Molecular weights can be measured by methods known in the art, including gel permeation chromatography, viscosity, light-scattering, among other methods.

The polymer of the polymer body can be formulated so as to degrade within a desired time interval, once present in a subject, or a biological medium. In some aspects, the time interval can be from about less than one day to about 1 month. Longer time intervals can extend to 6 months, including for example, polymers that degrade from about ≥0 to about 6 months, or from about 1 to about 6 months. In other aspects, the polymer can degrade in longer time intervals, up to 2 years or longer, including, for example, from about ≥0 to about 2 years, or from about 1 month to about 2 years.

The desired bioactive agent release mechanism can influence the selection of the polymer and/or the selection of each implant device or portion thereof, as discussed above. A biocompatible polymer, for example, can be selected so as to release or allow the release of a bioactive agent therefrom at a desired lapsed time after the implant device has been implanted in a subject. For example, the polymer can be selected to release or allow the release of the bioactive agent prior to the bioactive agent beginning to diminish its activity, as the bioactive agent begins to diminish in activity, when the bioactive agent is partially diminished in activity, for example at least 25%, at least 50% or at least 75% diminished, when the bioactive agent is substantially diminished in activity, or when the bioactive agent is completely gone or no longer has activity.

Examples of suitable polymers include without limitation polyesters, polyhydroxyalkanoates, polyhydroxybutyrates, polydioxanones, polyhydroxyvalerates, polyanhydrides, polyorthoesters, polyphosphazenes, polyphosphates, polyphosphoesters, polydioxanones, polyphosphoesters, polyphosphates, polyphosphonates, polyphosphates, polyhydroxyalkanoates, polycarbonates, polyalkylcarbonates, polyorthocarbonates, polyesteramides, polyamides, polyamines, polypeptides, polyurethanes, polyalkylene alkylates, polyalkylene oxalates, polyalkylene succinates, polyhydroxy fatty acids, polyacetals, polycyanoacrylates, polyketals, polyetheresters, polyethers, polyalkylene glycols, polyalkylene oxides, polyethylene glycols, polyethylene oxides, polypeptides, polysaccharides, or polyvinyl pyrrolidones. Other non-biodegradable but durable polymers include without limitation ethylene-vinyl acetate co-polymer, polytetrafluoroethylene, polypropylene, polyethylene, and the like. Likewise, other suitable non-biodegradable polymers include without limitation silicones and polyurethanes.

The implant device can comprise a variety of polysaccharides such as cellulose, modified cellulose including ethyl cellulose, hydroxyethyl cellulose, hydroxypropyl cellulose, methylcellulose, or hydroxypropylmethyl cellulose. The implant device can also comprise amylase, starch, maltodextrin, glycogen, chitin, or modified polysaccharides such as hydrophobically-modified polysaccharides. Examples of hydrophobically-modified polysaccharides include maltodextrins that have been hydrophobically-modified with $C_1$-$C_{10}$ alkyl sidechains, saturated sidechains, unsaturated sidechains, fatty acid side chains, or the like.

Other specific examples of suitable polymers include CAMEO polymers (ester-amide polymers), POLYACTIVE polymers, and SYNBIOSYS polymers (ester-urethane polymers). Further examples include polyesters with or without side-chains including poly(glycolide), poly(lactide), which has a pendent methyl group, and glycolides having $C_2$-$C_{12}$ side chains, such as hexyl-modified glycolide.

Further specific examples of suitable polymers include one or more of a poly(lactide), a poly(glycolide), a poly(lactide-co-glycolide), a poly(caprolactone), a poly(orthoester), a poly(phosphazene), a poly(hydroxybutyrate) or a copolymer containing a poly(hydroxybutarate), a poly(lactide-co-caprolactone), a polycarbonate, a polyesteramide, a polyanhydride, a poly(dioxanone), a poly(alkylene alkylate), a copolymer of polyethylene glycol and a polyorthoester, a biodegradable polyurethane, a poly(amino acid), a polyamide, a polyesteramide, a polyetherester, a polyacetal, a polycyanoacrylate, a poly(oxyethylene)/poly(oxypropylene) copolymer, polyacetals, polyketals, polyphosphoesters, polyhydroxyvalerates or a copolymer containing a polyhydroxyvalerate, polyalkylene oxalates, polyalkylene succinates, poly(maleic acid), and copolymers, terpolymers, combinations, or blends thereof.

When a block copolymer is desired, examples of useful biodegradable polymers are those that comprise one or more blocks of hydrophilic or water soluble polymers, including, but not limited to, polyethylene glycol, (PEG), or polyvinyl pyrrolidone (PVP), in combination with one or more blocks another biocompabible or biodegradable polymer that comprises lactide, glycolide, caprolactone, or a combination thereof.

In a preferred aspect, useful biocompatible polymers are those that comprise one or more residues of lactic acid, glycolic acid, lactide, glycolide, caprolactone, hydroxybutyrate, hydroxyvalerates, dioxanones, polyethylene glycol (PEG), polyethylene oxide, or a combination thereof. In a still further aspect, useful biocompatible polymers are those that comprise one or more residues of lactide, glycolide, caprolactone, or a combination thereof.

Lactide-based polymers can comprise any lactide residue, including all racemic and stereospecific forms of lactide, including, but not limited to, L-lactide, D-lactide, and D,L-lactide, or a mixture thereof. Useful polymers comprising lactide include, but are not limited to poly(L-lactide), poly (D-lactide), and poly(DL-lactide); and poly(lactide-co-glycolide), including poly(L-lactide-co-glycolide), poly(D-lactide-co-glycolide), and poly(DL-lactide-co-glycolide); or copolymers, terpolymers, combinations, or blends thereof. Lactide/glycolide polymers can be conveniently made by melt polymerization through ring opening of lactide and glycolide monomers. Additionally, racemic DL-lactide, L-lactide, and D-lactide polymers are commercially available. The L-polymers are more crystalline and resorb slower than DL-polymers. In addition to copolymers comprising glycolide and DL-lactide or L-lactide, copolymers of L-lactide and DL-lactide are commercially available. Homopolymers of lactide or glycolide are also commercially available.

In a particular aspect, when the biodegradable polymer is poly(lactide-co-glycolide), or a mixture of poly(lactide) and poly(glycolide), the amount of lactide and glycolide in the polymer can vary. In a further aspect, the biodegradable polymer contains 0 to 100 mole %, 40 to 100 mole %, 50 to 100 mole %, 60 to 100 mole %, 70 to 100 mole %, or 80 to 100 mole % lactide and from 0 to 100 mole %, 0 to 60 mole %, 10 to 40 mole %, 20 to 40 mole %, or 30 to 40 mole % glycolide, wherein the amount of lactide and glycolide is 100 mole %. In a further aspect, the biodegradable polymer can be poly(lactide), 95:5 poly(lactide-co-glycolide) 85:15 poly(lactide-co-glycolide), 75:25 poly(lactide-co-glycolide), 65:35 poly(lactide-co-glycolide), or 50:50 poly(lactide-co-glycolide), where the ratios are mole ratios.

In another aspect, the polymer can be a poly(caprolactone) or a poly(lactide-co-caprolactone). In one aspect, the polymer can be a poly(lactide-caprolactone), which, in various aspects, can be 95:5 poly(lactide-co-caprolactone), 85:15 poly(lactide-co-caprolactone), 75:25 poly(lactide-co-caprolactone), 65:35 poly(lactide-co-caprolactone), or 50:50 poly(lactide-co-caprolactone), where the ratios are mole ratios.

The bioactive agent used with the implant device is not critical, and a large variety of bioactive agents can be used. Typically, the bioactive agent is one that can be released from the implant device or portion thereof, usually as the device degrades or bioerodes, but can also release through a simple diffusion mechanism, or other mechanism. In one aspect, the processing of the polymer and bioactive agent can be performed under conditions such that the agent is intimately mixed or dispersed throughout the polymer, e.g., homogenously or substantially homogenously. Alternatively, the processing of the polymer and bioactive agent can be performed under conditions such that the agent is localized on or in only a portion or portions of the polymer body or implant device. Thus, the polymer can include areas that are rich in bioactive agent, and areas that are not as rich. The implant device can comprise a large number of bioactive agents either singly or in combination.

Various forms of the bioactive agent can be used, which are capable of being released from polymer into adjacent tissues or fluids. To that end, a liquid or solid bioactive agent can be incorporated into the implants described herein. The bioactive agents are at least very slightly water soluble, and preferably moderately water soluble. The bioactive agents can include salts of the active ingredient. As such, the bioactive agents can be acidic, basic, or amphoteric salts. They can be nonionic molecules, polar molecules, or molecular complexes capable of hydrogen bonding. The bioactive agent can be included in the compositions in the form of, for example, an uncharged molecule, a molecular complex, a salt, an ether, an ester, an amide, polymer drug conjugate, or other form to provide the effective biological or physiological activity.

Examples of bioactive agents that incorporated into systems herein include, but are not limited to, peptides, proteins such as hormones, enzymes, antibodies, antibody fragments, antibody conjugates, nucleic acids such as aptamers, iRNA, siRNA, DNA, RNA, antisense nucleic acid or the like, antisense nucleic acid analogs or the like, VEGF inhibitors, macrocyclic lactones, dopamine agonists, dopamine antagonists, low-molecular weight compounds, or high-molecular-weight compounds. Bioactive agents contemplated for use in the disclosed implants include anabolic agents, antacids, anti-asthmatic agents, anti-cholesterolemic and anti-lipid agents, anti-coagulants, anti-convulsants, anti-diarrheals, anti-emetics, anti-infective agents including antibacterial and antimicrobial agents, anti-inflammatory agents, anti-manic agents, antimetabolite agents, anti-nauseants, anti-neoplastic agents, anti-obesity agents, anti-pyretic and analgesic agents, antispasmodic agents, anti-thrombotic agents, anti-tussive agents, anti-uricemic agents, anti-anginal agents, antihistamines, appetite suppressants, biologicals, cerebral dilators, coronary dilators, bronchiodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, uterine relaxants, vitamins, or antigenic materials.

Other bioactive agents include androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestryramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines.

Representative drugs that can be used as bioactive agents in the implants include, but are not limited to, peptide drugs, protein drugs, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anticholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, antihypertensive agents, β-adrenergic blocking agents, nutritional agents, and the benzophenanthridine alkaloids. The agent can further be a substance capable of acting as a stimulant, sedative, hypnotic, analgesic, anticonvulsant, and the like.

Other bioactive agents include but are not limited to analgesics such as acetaminophen, acetylsalicylic acid, and the like; anesthetics such as lidocaine, xylocaine, and the like; anorexics such as dexadrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erythromycin, clindamycin, isoniazid, rifampin, and the like; antifungals such as amphotericin B, nystatin, ketoconazole, and the like; antivirals such as acyclovir, amantadine, and the like; anticancer agents such as cyclophosphamide, methotrexate, etretinate, and the like; anticoagulants such as heparin, warfarin, and the like; anticonvulsants such as phenyloin sodium, diazepam, and the like; antidepressants such as isocarboxazid, amoxapine, and the like; antihistamines such as diphenhydramine HCl, chlorpheniramine maleate, and the like; hormones such as insulin, progestins, estrogens, corticoids, glucocorticoids, androgens, and the like; tranquilizers such as thorazine, diazepam, chlorpromazine HCl, reserpine, chlordiazepoxide HCl, and the like; antispasmodics such as belladonna alkaloids, dicyclomine hydrochloride, and the like; vitamins and minerals such as essential amino acids, calcium, iron, potassium, zinc, vitamin $B_{12}$, and the like; cardiovascular agents such as prazosin HCl, nitroglycerin, propranolol HCl, hydralazine HCl, pancrelipase, succinic acid dehydrogenase, and the like; peptides and proteins such as LHRH, somatostatin, calcitonin, growth hormone, glucagon-like peptides, growth releasing factor, angiotensin, FSH, EGF, bone morphogenic protein (BMP), erythopoeitin (EPO), interferon, interleukin, collagen, fibrinogen, insulin, Factor VIII, Factor IX, Enbrel®, Rituxan®, Herceptin®, alpha-glucosidase, Cerazyme/Ceredose®, vasopressin, ACTH, human serum albumin, gamma globulin, structural proteins, blood product proteins, complex proteins, enzymes, antibodies, monoclonal antibodies, and the like; prostaglandins; nucleic acids; carbohydrates; fats; narcotics such as morphine, codeine, and the like, psychotherapeutics; anti-malarials, L-dopa, diuretics such as furosemide, spironolactone, and the like; antiulcer drugs such as rantidine HCl, cimetidine HCl, and the like.

The bioactive agent can also be an immunomodulator, including, for example, cytokines, interleukins, interferon, colony stimulating factor, tumor necrosis factor, and the like; allergens such as cat dander, birch pollen, house dust mite, grass pollen, and the like; antigens of bacterial organisms such as *Streptococcus pneumoniae, Haemophilus influenzae, Staphylococcus aureus, Streptococcus pyrogenes, Corynebacterium diphteriae, Listeria monocytogenes, Bacillus anthracis, Clostridium tetani, Clostridium botulinum, Clostridium perfringens. Neisseria meningitides, Neisseria gonorrhoeae, Streptococcus mutans. Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgddorferi, Campylobacter jejuni*, and the like; antigens of such viruses as smallpox, influenza A and B, respiratory synctial, parainfluenza, measles, HIV, SARS, varicella-zoster, herpes simplex 1 and 2, cytomeglavirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcuc neoformans, Histoplasma capsulatum, Candida albicans, Candida tropicalis, Nocardia asteroids, Rickettsia ricketsii, Rickettsia typhi, Mycoplasma pneumoniae, Chlamyda psittaci, Chlamydia trachomatis, Plasmodium falciparum, Trypanasoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

In a further specific aspect, the bioactive agent comprises an antibiotic. The antibiotic can be, for example, one or more of Amikacin, Gentamicin, Kanamycin, Neomycin, Netilmicin, Streptomycin, Tobramycin, Paromomycin, Ansamycins, Geldanamycin, Herbimycin, Carbacephem, Loracarbef, Carbapenems, Ertapenem, Doripenem, Imipenem/Cilastatin, Meropenem, Cephalosporins (First generation), Cefadroxil, Cefazolin, Cefalotin or Cefalothin, Cefalexin, Cephalosporins (Second generation), Cefaclor, Cefamandole, Cefoxitin, Cefprozil, Cefuroxime, Cephalosporins (Third generation), Cefixime, Cefdinir, Cefditoren, Cefoperazone, Cefotaxime, Cefpodoxime, Ceftazidime, Ceftibuten, Ceftizoxime, Ceftriaxone, Cephalosporins (Fourth generation), Cefepime, Cephalosporins (Fifth generation), Ceftobiprole, Glycopeptides, Teicoplanin, Vancomycin, Macrolides, Azithromycin, Clarithromycin, Dirithromycin, Erythromycin, Roxithromycin, Troleandomycin, Telithromycin, Spectinomycin, Monobactams, Aztreonam, Penicillins, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Polypeptides, Bacitracin, Colistin, Polymyxin B, Quinolones, Ciprofloxacin, Enoxacin, Gatifloxacin, Levofloxacin, Lomefloxacin, Moxifloxacin, Norfloxacin, Ofloxacin, Trovafloxacin, Sulfonamides, Mafenide, Prontosil (archaic), Sulfacetamide, Sulfamethizole, Sulfanilimide (archaic), Sulfasalazine, Sulfisoxazole, Trimethoprim, Trimethoprim-Sulfamethoxazole (Cotrimoxazole) (TMP-SMX), Tetracyclines, including Demeclocycline, Doxycycline, Minocycline, Oxytetracycline, Tetracycline, and others; Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in U.S.), Timidazole, Ropinerole, Ivermectin, Moxidectin, Afamelanotide, Cilengitide, or a combination thereof. In one aspect, the bioactive agent can be a combination of Rifampicin (Rifampin in U.S.) and Minocycline.

The amount of drug incorporated into the implant device varies depending upon a particular drug, the desired therapeutic affect and the desired time span. Since a variety of devices in a variety of sizes and shapes are intended to provide dosage regimens for therapy for a variety purposes, there is no critical upper limit in the amount of drug incorporated into the device. The lower limit too will depend upon the activity of the drug and the time span of its release from the device. Those skilled in the pharmaceutical arts will know how to determine toxic levels of a given drug as well as the minimum effective dose.

It is contemplated that other components such as, for example, excipients, pharmaceutically carriers or adjuvants, microparticles, and the like, can be combined with the polymer and/or the bioactive agent. Thus, in certain aspects, the bioactive agent can be present as a component in a pharmaceutical composition. Pharmaceutical compositions can be conveniently prepared in a desired dosage form, including, for example, a unit dosage form or controlled release dosage form, and prepared by any of the methods well known in the art of pharmacy. In general, pharmaceutical compositions are prepared by uniformly and intimately bringing the bioactive agent into association with a liquid carrier or a finely divided solid carrier, or both. The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. Other pharmaceutically acceptable carriers or components that can be mixed with the bioactive agent can include, for example, a fatty acid, a sugar, a salt, a water-soluble polymer such as polyethylene glycol, a protein, polysachamide, or carboxmethyl cellulose, a surfactant, a plasticizer, a high- or low-molecular-weight porosigen such as polymer or a salt or sugar, or a hydrophobic low-molecular-weight compound such as cholesterol or a wax.

The polymer and bioactive agent can be co-processed by a variety of techniques, such as, for example, melt extruding, injection molding, compression molding, or roller compacting the admixture into a desired shape or structure, as will be discussed below. In certain aspects, the polymer and bioactive agent are combined or admixed to form a blend or admixture. Admixing methods can be performed using techniques known in the art. For example, the polymer and bioactive agent can be dry blended (i.e., mixing of particulates of the polymer and the agent) using, for example, a Patterson-Kelley V-blender, or granulated prior to processing.

To prepare the implant device from the polymer, a variety of methods can be used. In a preferred aspect, the implants are prepared by extrusion methods, for example through heat extrusion or solvent extrusion. The bioactive agent and polymer can first be blended, for example using a Turbula Shaker Mixer Type T2 F (available from a number of commercial sources, including Artisan Scientific Corporation 301 E. Mercury Drive Champaign, Ill. 61822). The blend can be dried, formed into a film, or formed into another appropriate solid and subsequently extruded. The bioactive agent and the polymer can also be added separately to the extruder and subsequently combined and blended during the extrusion process.

The blend can be extruded using a suitable plastometer, for example, a Tinius Olsen Model UE-4-78 melt plastometer (available from Tinius Olsen Corporation, 1065 Easton Road, PO Box 1009, Horsham, Pa. 19044-8009). Other suitable extruders use in the pharmaceutical arts can also be used. Examples include single-screw extruders, such as a RAND-CASTLE extruder (Cedar Grove, N.J., U.S.A.), twin-screw extruders, or even combinations of two or more extruders. The implant device can be prepared using a single pass through an extruder, or extrusion can be performed multiple times to further blend and/or process the bioactive agent and the polymer mixture. Additionally, molding techniques can also be used to prepare the implant devices, including for example, injection molding, compression molding, and the like.

The extruded formulation can also be prepared by the "drawing" technique, wherein the extruded article is pulled or "drawn" out at a rate that is slightly faster than the actual rate of extrusion. This drawing action can orient the polymer (and can possibly induce crystallization in certain polymers) which can affect release characteristics of that formulation.

After extrusion, the implant device can be further processed. In one aspect, multiple implant devices can be prepared from a single extruded article by cutting the extruded article into more than one segment. When the bioactive agent is homogenously distributed in the extruded article, the size of the segment of the extruded article will determine the amount of bioactive agent in that segment and will therefore affect the release profile of the segment. The surface area of the segment will also likewise affect the release profile of the bioactive agent.

In a further aspect, multiple implant devices can be prepared from a single extruded article by cutting the extruded article into a plurality of disconnected segments and the plurality of segments can then be administered to a subject. The release profile of the plurality of segments, in this aspect, can be affected by size, surface area, and surface treatment (if any), among other variables. For example, if a single extruded article is cut into a 1 cm, 2 cm, and 3 cm segments, the release profile exhibited by the cut segments will be different than a release profile exhibited by the single extruded article (6 cm) and will also likely be different than three 3 cm segments prepared from the same 6 cm extruded article. It will be apparent however, in other aspects, that the plurality of implant devices can comprise individual implant devices prepared from more than one extruded article.

In one aspect, modular polymer body portions can be used, such that one or more portions can be adjoined together. In this aspect, multiple extruded implant articles can be connected. Preferably, the adjoined implant devices are not adjoined only through a coaxial configuration, wherein one portion forms a sheath around a core. However, the core/sheath arrangement can be used provided that at least one further arrangement is present, for example, if two implant device segments form a core/sheath having two ends and one or more additional implant devices are connected to at least one of the ends, wherein at least one of the additional implant devices is not formed in a core/sheath arrangement. In a further aspect, when the implant device is a rod having two ends, one or more of the ends can be connected to the end of another implant device. A variety of methods for adjoining individual implant devices can be used, for example, through the use of biocompatible or biodegradable adhesives, through melt processing, thermal annealing, solvent annealing, solution processing, among other methods.

In another similar aspect, the implant device can comprise different polymer body portions that have been co-manufacturing to form a single composite article. A variety of arrangements can be prepared according to this aspect, including for example a polymer body or portion thereof having more than one cross-section when viewed perpendicular to the elongated axis, and/or a core sheath or other suitable arrangement, as will be discussed below. Preferably, two or more polymer bodies are co-extruded together to form a composite implant device. As discussed above, at least two the polymer body portions in this aspect exhibit a different release profile.

Various extrusion methods can be used to prepare implant devices comprising co-extruded polymer bodies. For an implant device having more than one cross-sections when viewed from an end of the implant device, wherein each section which comprises a polymer portion, can be formed by simultaneously delivering a portion of extrudate from one extruder and a portion of extrudate from another extruder and then joining the two or more portions near a die-head outlet. For an implant device having two or more polymer body portions adjoined at their ends (segments), two or more extruders can deliver polymer from a feed source to a die-head that can then produce a single-stranded article by switching between the feed sources of the two or more extruders. For a core/sheath arrangement or other similar arrangement, typical coaxial extrusion methods can be used, wherein two or more polymer body portions are extruded at the same time. According to this arrangement, a coaxial die-head can be used that forms the interior portion or core then the die-head passes extrudate from another extruder around the core thereby forming the outer sheath.

Figure 1A:
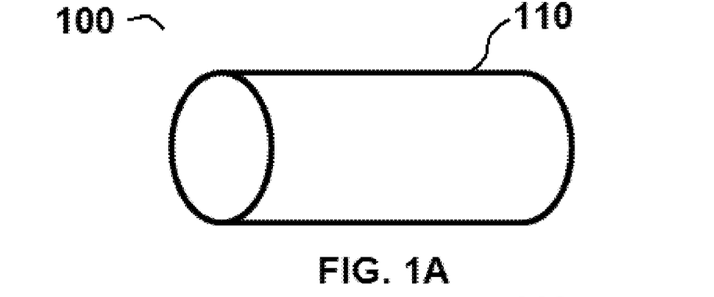
FIGS. 1A-C are drawings of exemplary implant devices.
Figure 1B:
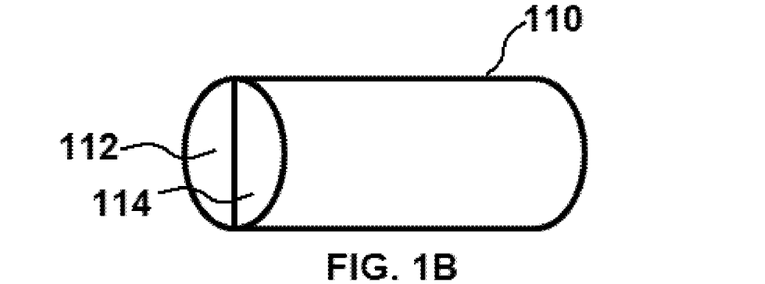
Figure 1C:
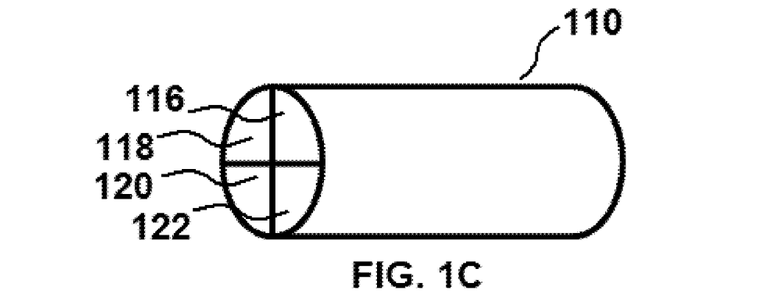
Figure 2A:
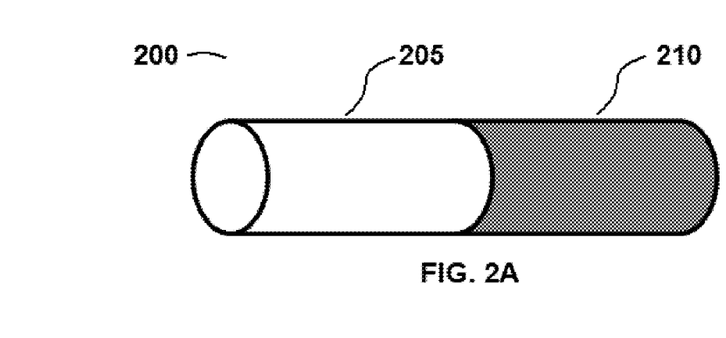
FIGS. 2A-D are drawings of exemplary implant devices comprising adjoined polymer bodies.
Figure 2B:
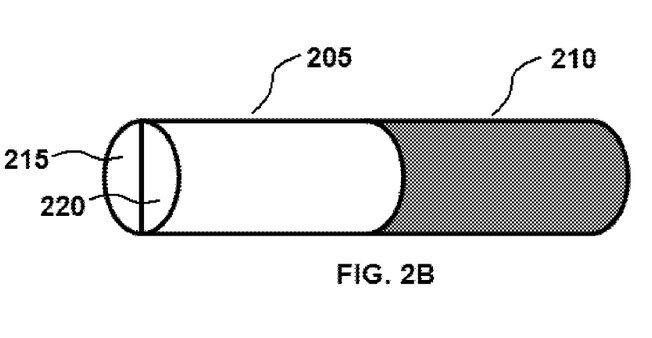
Figure 2C:
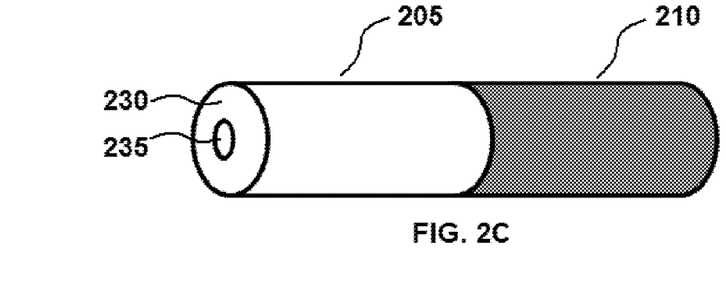
Figure 2D:
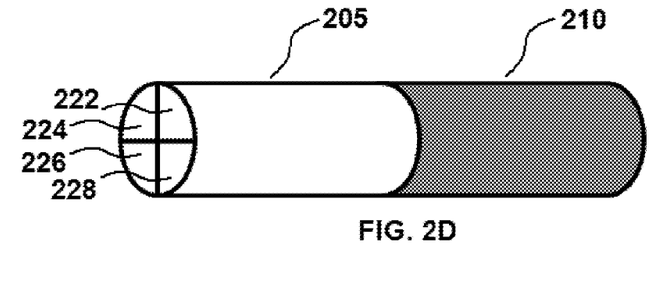

The precise shape of the implant device will depend on a variety of factors including the desired therapeutic effect, the intended physiological environment for the implant device, the surgical procedure and convenience. According to various aspects, however, the implant device can be in the shape of a rod, a fiber, a cylinder, a bead, a ribbon, a disc, a wafer, a free-formed shaped solid, or a variety of other shaped solids. The device can have any regular or irregular shape and can have any cross section such as circular, rectangular, triangular, oval, bilobe, trilobe, cloverleaf, c-shaped, pie-slice, crescent-moon, and the like. In a specific aspect, the implant device is in the shape of a rod having an elongated body and two ends. With reference to FIG. 1, for example, a variety of rod-shaped implant devices 100 can be used. According to FIG. 1A, a substantially homogenous implant device 100 comprising a single polymer body having one portion 110 can be used with one or more other implant devices that provide a different release profile. According to FIG. 1B and FIG. 1C, an implant device 100 comprising a polymer body 110 having two cross-sectional portions (112, 114), or four cross-sectional portions (116, 118, 120, 122) can be used. Such devices can be made according to the extrusion methods discussed above. Preferably, when an implant device comprises at least two cross-sectional portions, at least one portion exhibits a different release profile than another.

With reference to FIG. 2, an implant device 200 can comprise two or more polymer body portions that are adjoined. Such implant devices can be prepared by either connecting two or more modular portions, or by co-manufacturing, for example co-extruding, two or more portions together. With reference to FIG. 2A, for example, two rod-segments of a polymer body (205, 210) can be adjoined at their respective ends. With reference to FIGS. 2B-2D, such an end-to-end arrangement can also be used in combination with implant device segments that are different cross-sectionally, for example a segment having two or more cross sections (FIG. 2B, 215, 220 and FIG. 2D, 222, 224, 226, 228) or a portion having a core 235 surrounded by a sheath 230, as shown in FIG. 2C. One or more portions or sections of the implant device, as discussed above, can exhibit a different release profile than another portion or section.

Generally, the size of the implant device will depend on its intended use, and as such will vary. For implant devices that will be used primarily for drug-delivery, for example, and will be administered through an injection device, the implant device will be so-sized as to fit within an injection device, such as a trochar (e.g., in the centimeter range). The size of each implant device in a plurality can affect the amount and therefore the release profile of the bioactive agent, as discussed above. Thus, the size of an implant device can be selected to provide a desired release profile. The precise shape of implant device for the kit will depend on a variety of factors including the desired therapeutic effect, the intended physiological environment for the implantable article, the surgical procedure and convenience.

The disclosed implant devices can be used in combination with virtually any further implant processing method. Thus, one or more surfaces of the implant device can be coated with a coating composition. The coating composition can further comprise other ingredients, such as other bioactive agents, additives, and the like, including for example, salts, sugars, polysaccharides, water-soluble additives, non-water-soluble additives, partially water-soluble additives water-soluble polymers, non-water soluble polymers, and partially water-soluble polymers, among others.

The implant devices can also be solvent-treated on at least a portion, or all, of the implant device surface. Solvent-treatment methods for implant devices are described in Tice et al. "Methods for manufacturing delivery devices and devices thereof" U.S. Patent Application Publication No. 20060029637, which is incorporated herein by the this reference in its entirety, for its teachings of solvent-treatment methods. In various aspects, the implant device can be treated on only a portion of the device surface, such as the end or the longitudinal side of the implant device. In further aspects, a plurality of implant devices can comprise one or more implant devices that have been solvent-treated, and one or more implant devices that have not been solvent treated, and/or one or more implant devices that have been solvent treated in a different way, e.g. on a different portion or with a different solvent or solvent solution. Various combinations of solvent-treatment protocols can also be used to further tailor the release profiles of the implant devices. When an implant device is solvent-treated, the solvent used to treat the implant devices can contain only solvent or can contain a polymer or another substance that will coat at least a portion of the implant device after the solvent-treatment. Thus, in some aspects, the implant devices can be dip-coated using solvent-treatment methods.

In a preferred aspect, a plurality of implant devices, wherein at least two of the implant devices differ by release profile, are used to provide a desired cumulative release profile. In one specific aspect, two or more implant devices prepared from singly extruded rods are used together to provide a desired cumulative release profile. The plurality of implant devices can be used as a single mixture, for example an injectable composition comprising the plurality, or as separate implants, for example implants to be injected separately.

In one aspect, a plurality of implant devices can be present in a kit. The implant devices of the kit can each comprise a single or multiple polymer bodies, provided that at least two of the implant devices in the kit exhibit a different release profile. The kit can comprise a suitable package or container for the implant devices. Examples include without limitation sterile packaging. In a further aspect, a kit can include a prepackaged injection device, comprising an injection device that is loaded with the implant devices. Suitable injection devices include without limitation syringes, trochars, and others.

The kit can also comprise a composition containing the implant devices, such as a pharmaceutical composition, as discussed above in reference to the bioactive agent. Any of those aforementioned pharmaceutical compositions can be used to contain or provide a medium for delivering the implant devices into a subject.

As discussed above, the implant devices are used to administer a bioactive agent to a subject in need thereof, for example to treat a disorder for which the bioactive agent can effective. The implant devices can be administered to any tissue or fluid of a subject. Likewise, the mode of administration can be any suitable mode, for example subcutaneous injection, oral administration, and the like. The number of implant devices to be administered will generally be selected based on the desired dosage of the bioactive agent, which will vary greatly depending on the disorder but can be readily determined by one in the pharmaceutical arts.

The implant device can be implanted in any desired subject. The subject can be a vertebrate, such as a mammal, a fish, a bird, a reptile, or an amphibian. The subject of the herein disclosed methods can be, for example, a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered.

Bioactive agents can be administered to subjects using according to various methodologies for which the present invention provides advantages. For example, the disclosed implant devices can be used in subjects that were previously treated through dose-titrations using oral forms of a bioactive agent in order to reach a desired steady-state drug pharmacokinetic level that adequately treats the disorder. One of skill in the art can use such prior dose-titration information to formulate an implant device or plurality of implant devices that provides the requisite release profile. Thus, the oral dose-titration information, along with known oral bioavailability values, can be used to estimate the equivalent dose-rate needed from implant formulations in order to reach the same (or similar) pharmacokinetic levels. Using such a predetermined target dose level, combinations of multiple implants can be selected and administered to the subject in order to achieve the desired target dose rate level that is needed to address the form and/or severity of their disorder.

Alternatively, dose-titration studies can be performed using the implant formulations themselves (e.g. using a plurality of implant devices). According to this aspect, initial rounds of dosings can be performed along while monitoring plasma pharmacokinetic levels, whereas successive dosings can be performed using different combinations of implants, or combinations of portions of an implant, or both, in order to achieve the desired steady-state drug pharmacokinetic levels that adequately treat the disorder. Once a suitable implant formulation is identified that provides for the desired steady-state drug levels, this formulation can be used in subsequent rounds of dosing for a long-term treatment, or for a treatment of a chronic disorder.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The formulations discuss below could be administered by a variety of methods, including subcutaneous implantation of the implant device, or by injection the implant device into the subject, such as in the blood-stream of the subject. The release profiles could be generated by monitoring blood or plasma levels for the bioactive agent using, for example, liquid chromatography (LC), mass spectroscopy (MS), or combined LC-MS methods.

Example 1

Preparation of Implant Devices

The specific implant devices discussed below were made with the bioactive agent Gosserelin Acetate. Each of the following formulations was blended using a Turbula Shaker Mixer Type T2 F. The blending was done at a setting of 0.67 for twenty minutes for each blend. The blends were then extruded using a Tinius Olsen Model UE-4-78 melt plastometer. The Tinius Olsen is a solid block of steel about 80 mm in diameter and about 160 mm high/long with a hollow core about 13 mm in diameter. The discharge of the core has a shoulder that allows different size dies to be used based on the desired diameter of extruded rod. For the Examples below, a 1.2-mm die was used, meaning that the core of the die was 1.2 mm in diameter. The main block of the Tinius Olsen has heater bands encased by insulation and a shroud that allows the Tinius Olsen to be heated to desired temperatures. A thermocouple was used to measure the temperature of the block. The control system then uses the thermocouple values to either turn the heater bands on or off. Throughout the extrusion process, the heater bands will switch off and on to maintain the desired temperature. The blend, approximately 2 grams in each instance, was loaded into the Tinitus Olsen which had been equilibrated to 90° C. A charging rod was placed in the core of the Tinius Olsen to compress the blend and a weight was placed on the end of the charging rod to aid in the compaction of the blend. The blend was equilibrated. After an extrusion load was placed on the charging rod, the plug was removed from the discharge area to begin the extrusion run. The 2-gram charge afforded segments of extruded rod.

Formulation A

Implant Formulation A was made with bioactive agent and a poly(DL-lactide). The poly(DL-lactide) had an inherent viscosity of 0.26 dL/g, measured at 30° C. with 0.5 gm/dL polymer concentration in chloroform. The desired bioactive agent content in the implant was 5 wt % Gosserelin Acetate. The extruded rod from Formulation A was cut so that each implant would contain 1 mg of bioactive agent.

Formulation B

Implant Formulation B was made with bioactive agent and an 85:15 poly(DL-lactide-co-glycolide). The poly(DL-lactide-co-glycolide) had an inherent viscosity of 0.37 dL/g, measured at 30° C. with 0.5 gm/dL polymer concentration in chloroform. The desired bioactive agent content in the implant was 5 wt % Gosserelin Acetate. The extruded rod from Formulation B was cut so that each implant would contain 1 mg of bioactive agent.

Formulation C

Implant Formulation C was made with bioactive agent and a poly(DL-lactide). The poly(DL lactide) had an inherent viscosity of 0.26 dL/g, measured at 30° C. with 0.5 gm/dL polymer concentration in chloroform. The desired bioactive agent content in the implant was 10 wt % Gosserelin Acetate. The extruded rod from Formulation C was cut to various lengths so that there were implants that contained 1 mg of bioactive agent, 2 mg of bioactive agent, and 4 mg of bioactive agent.

Formulation D

Implant Formulation D was made with bioactive agent and an 85:15 poly(DL-lactide-co-glycolide). The poly(DL-lactide-co-glycolide) had an inherent viscosity of 0.37 dL/g, measured at 30° C. with 0.5 gm/dL polymer concentration in chloroform. The desired bioactive agent content in the implant was 25 wt % Gosserelin Acetate. The extruded rod from Formulation D was cut to various lengths so that there were implants that contained 1 mg of bioactive agent, 2 mg of bioactive agent, and 4 mg of bioactive agent.

Formulation E

Implant Formulation E was made with bioactive agent and an 85:15 poly(DL-lactide-co-glycolide). The poly(DL-lactide-co-glycolide) had an inherent viscosity of 0.37 dL/g, measured at 30° C. with 0.5 gm/dL polymer concentration in chloroform. The desired bioactive agent content in the implant was 10 wt % Gosserelin Acetate. The extruded rod from Formulation E was cut to various lengths so that there were implants that contained 1 mg of bioactive agent, 2 mg of bioactive agent, and 4 mg of bioactive agent.

Formulation F

Implant Formulation F was made with bioactive agent and a poly(DL-lactide). The poly(DL-lactide) had an inherent viscosity of 0.26 dL/g, measured at 30° C. with 0.5 gm/dL polymer concentration in chloroform. The desired bioactive agent content in the implant was 25 wt % Gosserelin Acetate. The extruded rod from Formulation F was cut to various lengths so that there were implants that contained 1 mg of bioactive agent, 2 mg of bioactive agent, and 4 mg of bioactive agent.

Example 2

Same Loading with Different Polymer

Figure 3:
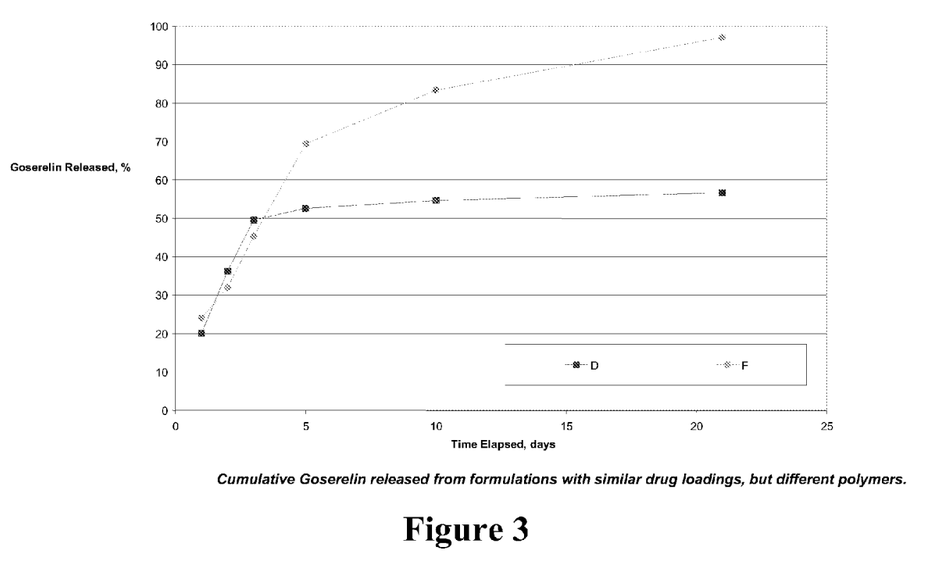
FIG. 3 is a plot showing cumulative Goserelin released from formulations with similar drug loadings, but different polymers.

To achieve a desired release profile of a bioactive agent, the polymer can be changed. An example of this is comparing Formulations D and F as described above. The release profiles of Formulations D and F are shown in FIG. 3.

Example 3

Different Loading with Same Polymer

Figure 4:
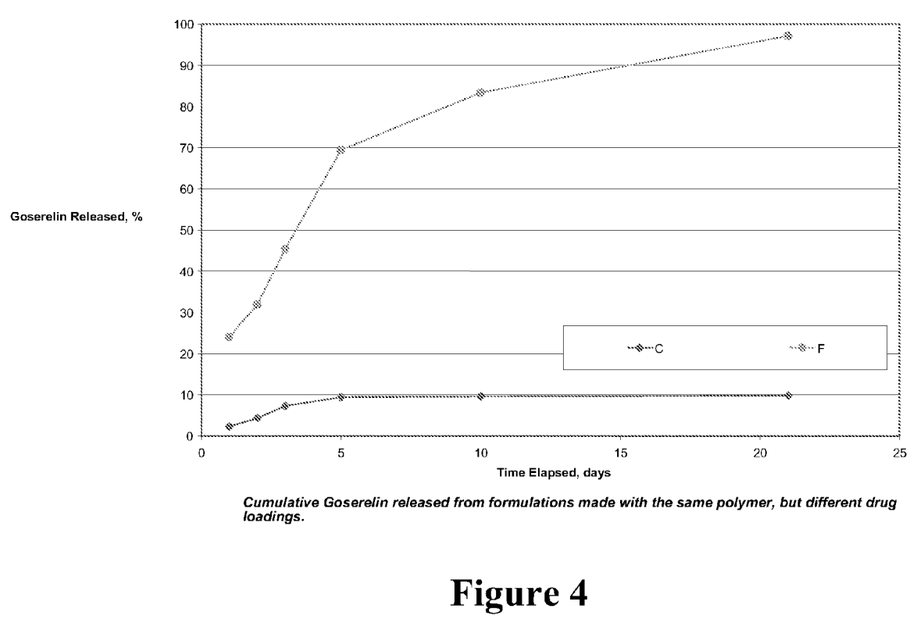
FIG. 4 is a plot showing cumulative Goserelin released from formulations made with the same polymer, but different drug loadings.

Another approach to achieving a desired release profile is to change to loading of bioactive agent in the implant. An example of this is comparing Formulations C and F as described above. The release profiles of Formulations C and F are shown in FIG. 4.

Example 3

Use of Multiple Implant Devices

Figure 5:
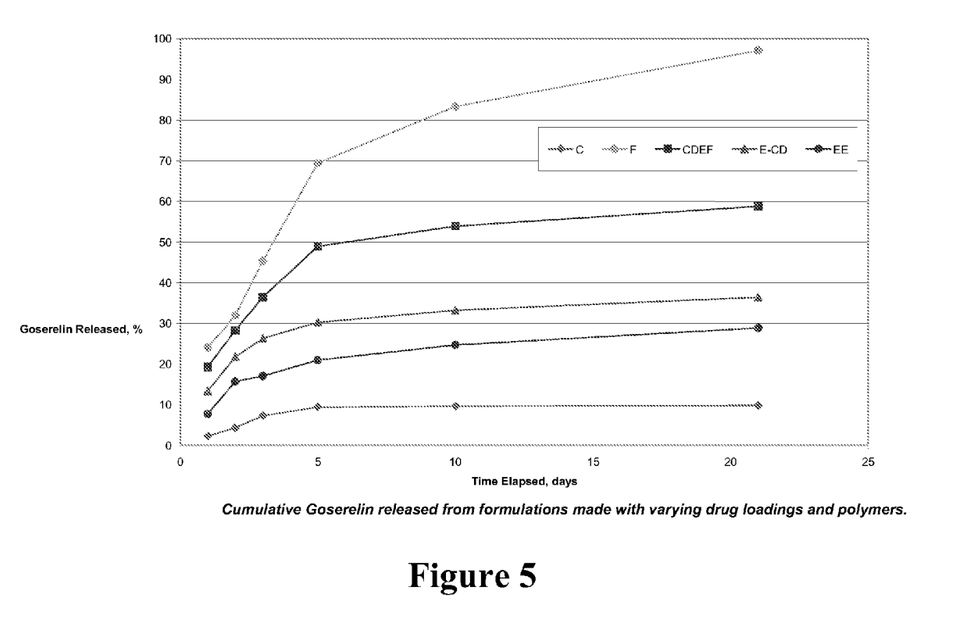
FIG. 5 is a plot showing cumulative Goserelin released from formulations made with varying drug loadings and polymers.
Figure 6:
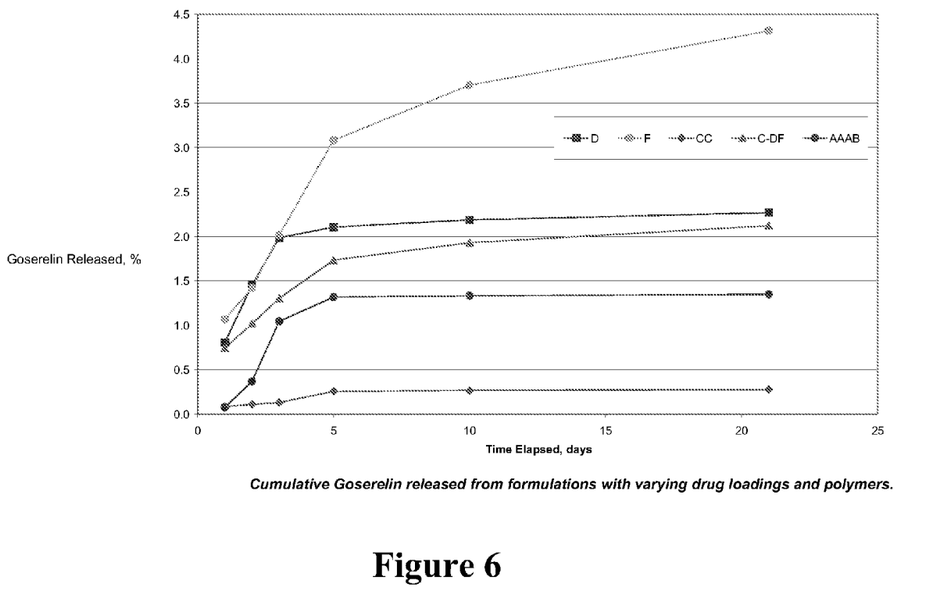
FIG. 6 is a plot showing cumulative Goserelin released from formulations with varying drug loadings and polymers

Different formulations can be used in varying quantities to form a dose of bioactive agent administered at one time (FIGS. 5, 6). FIG. 5 shows the release of Formulation C and Formulation F. The others shown on the graph in FIG. 5 all have 4 mg bioactive agent, but were generated by combining implants of different formulations. FIG. 6 uses Formulation D and Formulation F as the basis for comparison with different combinations. As evident in these graphs, the ability to manipulate release kinetics is greatly enhanced through the use of multiple implants.

Example 4

(Prophetic): Tailoring Dose

A set of implant formulations can be prepared that, individually, provide for different average daily release rates over approximately a 4 week period of time. Formulations 1, 2, and 3 provide for daily release rates of approximately 2, 4, and 8 micrograms drug per day for the 4-week period (respectively).

Patient 1 is known from prior experience (based on previous dose-titrations using oral versions of the drug) to require treatment with this drug at a level of approximately 8 micrograms drug per day to treat his particular form and severity of disease.

Patient 2 is known (based on similar prior experience) to require treatment at a level of 12 micrograms drug per day to treat his particular form and severity of disease.

Patient 3 is known (based on similar prior experience) to require treatment at a level of 14 micrograms drug per day to treat his particular form and severity of disease.

Using the present invention, Patient 1 could therefore be treated by administration of one dose of Formulation 3. Patient 2 could therefore be treated by administration of one dose of Formulation 2 and one dose of Formulation 3. Patient 3 could therefore be treated by administration of one dose of Formulation 1, one dose of Formulation 2 and one dose of Formulation 3. Formulations 1-3 can be provided by using combinations of implants, or implants having different polymer bodies or sections, as in FIG. 1B, 1C, FIGS. 2A-D, or both, as discussed above.

Various modifications and variations can be made to the compounds, composites, kits, articles, devices, compositions, and methods described herein. Other aspects of the compounds, composites, kits, articles, devices, compositions, and methods described herein will be apparent from consideration of the specification and practice of the compounds, composites, kits, articles, devices, compositions, and methods disclosed herein. It is intended that the specification and examples be considered as exemplary.

What is claimed is:

1. An implant device comprising a polymer body having at least two portions that each comprise a bioactive agent therein and/or on a surface thereof, the bioactive agent being releasable from the at least two adjoined portions, wherein a release profile characterizes the release of the bioactive agent from each of the portions and wherein at least two portions differ by release profile by releasing a different amount of the bioactive agent over time, provided that the portions are not adjoined only in a core-sheath configuration, and wherein the polymer body comprises at least two cross-sectional portions; wherein said implant device is in the form of a rod, where at least two cross-sectional portions having different release profiles are formed on one end of the rod; wherein the implant device has a cumulative release profile of the at least two portions and the at least two cross-sectional portions.

2. The implant device of claim 1, wherein the polymer body comprises four cross-sectional portions.

3. The implant device according to claim 1 wherein at least one portion of the at least two cross-sectional portions exhibits a different release profile than the other portion.

4. The implant device according to claim 1, wherein the polymer body comprises at least two segments.

5. The implant device of claim 4, wherein at least one of the segments is configured in a core-sheath arrangement and at least one other segment is configured in a non-core-sheath arrangement.

6. The implant device according to claim 1, wherein the polymer body is biodegradable.

7. A kit comprising a plurality of implant devices according to claim 1, wherein at least two of the implant devices in the kit exhibit a different release profile.

8. The kit of claim 7, wherein the plurality of implant devices are contained within a pharmaceutical carrier.

9. The kit of claim 7, further comprising an injection device for injecting the plurality of implant devices into a subject.

10. The kit of claim 9, wherein the plurality of implant devices are loaded into the injection device.

11. The kit of claim 7, wherein the at least two of the implants that differ by release profile comprise different biodegradable polymers, different amounts of bioactive agent, different bioactive agents, different sizes, different surface characteristics, or a combination thereof.

* * * * *